United States Patent [19]
Mossman et al.

[11] Patent Number: 6,028,211
[45] Date of Patent: Feb. 22, 2000

[54] COMPOSITION AND METHOD FOR REDUCING FOULING IN PROCESS EQUIPMENT USED FOR MANUFACTURING AROMATIC MATERIALS

[75] Inventors: Allen B. Mossman, Wheaton, Ill.; David A. Young, Decatur, Ala.; Paul K. Behrens, Warrenville; Juergen K. Holzhauer, Naperville, both of Ill.

[73] Assignee: BP Amoco Corporation, Chicago, Ill.

[21] Appl. No.: 09/022,693

[22] Filed: Feb. 12, 1998

Related U.S. Application Data

[60] Provisional application No. 60/041,765, Mar. 31, 1997.
[51] Int. Cl.⁷ .............................. C07C 69/76; C10G 9/16; A23L 1/00; C09K 15/32
[52] U.S. Cl. ................... 560/100; 208/48 AA; 252/383; 252/400.23; 560/77; 560/80; 560/99; 562/490
[58] Field of Search ............... 208/48 AA; 560/77, 560/80, 99, 100; 562/490; 252/400.23, 383

[56] References Cited

U.S. PATENT DOCUMENTS

| | | | |
|---|---|---|---|
| 3,492,219 | 1/1970 | Miller | 208/48 |
| 4,024,051 | 5/1977 | Shell et al. | 208/348 |
| 4,927,519 | 5/1990 | Forester | 208/48 |

FOREIGN PATENT DOCUMENTS

| | | |
|---|---|---|
| 51-63368 | 6/1976 | Japan . |
| 51-127036 | 11/1976 | Japan . |
| 56-14322 | 4/1981 | Japan . |
| 9310080 | 5/1993 | WIPO . |

*Primary Examiner*—Porfirio Nazario-Gonzalez
*Attorney, Agent, or Firm*—Scott P. McDonald; Stephen L. Hensley

[57] ABSTRACT

Methods for reducing the fouling of process equipment used in the manufacture of aromatic compounds such as dimethyl-2,6-naphthalenedicarboxylate are disclosed. The methods require treating manufacturing process streams with a metal complexing agent. Novel compositions useful in the manufacture of aromatic materials such as dimethyl-2,6-naphthalenedicarboxylate also are disclosed.

24 Claims, No Drawings

COMPOSITION AND METHOD FOR REDUCING FOULING IN PROCESS EQUIPMENT USED FOR MANUFACTURING AROMATIC MATERIALS

This application claims the priority of provisional U.S. patent application Ser. No. 60/041,765, filed on Mar. 31, 1997.

FIELD OF THE INVENTION

This invention relates generally to a method for reducing fouling in process equipment used for manufacturing aromatic materials such as dimethyl naphthalenedicarboxylates. More specifically, this invention relates to a method for reducing fouling in process equipment used for manufacturing aromatic materials such as dimethyl-2,6-naphthalenedicarboxylate by treating manufacturing process streams with one or more metal complexing compounds.

BACKGROUND OF THE INVENTION

Dimethyl-2,6-naphthalenedicarboxylate, or "NDC," is representative of a monomer that can be used to prepare a variety of polyester materials. For example, NDC can be condensed with ethylene glycol to form poly(ethylene-2,6-naphthalate), or "PEN," a high performance polyester material.

Fibers and films made from PEN have considerably improved strength and superior thermal properties relative to films and fibers made from poly(ethyleneterephthalate). PEN therefore is an exceptional material for preparing commercial articles such as thin films used for the manufacture of magnetic recording tape and electronic components. Additionally, because of PEN's superior resistance to the diffusion of gases such as carbon dioxide, oxygen and water vapor, films made from PEN particularly are useful for manufacturing articles such as "hot fill" food containers. PEN also is useful for preparing high strength fibers which can be used to manufacture items such as tire cord.

Processes for manufacturing NDC and other aromatic esters from aromatic acids are well known. For example, U.S. Pat. Nos. 5,254,719, 5,262,560 and 5,350,874 describe processes for manufacturing NDC from 2,6-naphthalenedicarboxylic acid or "NDA" by reacting NDA with methanol. These and other processes for manufacturing NDC and other aromatic esters typically involve one or more ester crystallization or recrystallization steps, as well as a distillation step where the aromatic ester is distilled, typically using a fractional distillation column, to prepare high purity esters suitable for preparing PEN and other polyesters.

Aromatic acids useful for preparing aromatic esters can be prepared in a number of ways. For example, NDA advantageously is obtained by oxidizing a suitable naphthalenic feedstock such as 2,6-dimethylnaphthalene. Such oxidation reactions typically are conducted in a liquid phase mixture using one or more heavy metal catalysts to catalyze the oxidation of the naphthalenic feedstock to NDA. One preferred method uses a mixture of cobalt and manganese catalyst metals in a liquid phase oxidation of 2,6-dimethylnaphthalene. This method uses a low molecular weight acid such as acetic acid as the reaction solvent and air as the source of oxygen for oxidizing the methyl groups on 2,6-dimethyinaphthalene to the carboxylic acid groups of NDA. One such process is discussed in detail in U.S. Pat. No. 5,183,933 to Harper et al., the disclosure of which is hereby incorporated by reference.

We have discovered that when NDA is prepared by such an oxidation process, the catalyst metals such as cobalt and manganese can cause severe fouling of the process equipment used to manufacture NDC from NDA. Process equipment exhibiting such fouling includes heat exchangers used to increase the temperature of a mixture of NDA and methanol for a subsequent esterification reaction, heat exchangers used to increase the temperature of a mixture of NDC, NDA, and methanol for a subsequent recrystallization, filter cloths on equipment used to recover NDC particles from methanol, heat exchangers used to heat and evaporate filtration mother liquor to recover solvent, the internal portions of the reactor and associated piping used in the esterification process, and the internals of NDC distillation columns.

Equipment such as that noted above may become encrusted or fouled with solid deposits which reduce the efficiency of the equipment. If operations continue under conditions that permit fouling, the equipment can become completely plugged or otherwise inoperative. Fouled equipment can substantially reduce plant production rates. Furthermore, when fouling becomes severe, production of NDC must be stopped to clean out the fouled equipment. Thus, manufacturers of aromatic materials such as NDC require a method to reduce or eliminate fouling of process equipment. Our invention provides such a method.

SUMMARY OF THE INVENTION

We have found that fouling problems in the production of aromatic materials from heavy metal-containing feedstocks can be drastically reduced by using a metal complexing agent during the production process. Use of metal complexing agents such as phosphorus salts has been found to increase the run time of process equipment such as heat exchangers and filters several fold, thereby dramatically increasing plant throughput and minimizing the need for fouling-related plant maintenance.

In a first embodiment of the invention, a method for reducing fouling in equipment used to process a metal-containing aromatic feedstock mixture requires treating a process stream of the aromatic feedstock mixture with a metal complexing compound.

The term "metal-containing aromatic feedstock mixture" refers to a mixture containing at least 5 parts by weight of an aromatic compound and between about 10–40,000 total parts per million of one or more heavy metals having atomic numbers from 21 to 82.

The term "metal complexing compound" means any compound that remains sufficiently stable under processing conditions to complex with the heavy metal or metals contained in an aromatic feedstock mixture to prevent fouling of the processing equipment. Such metal complexing compounds include, for example, phosphorus-containing compounds and other metal complexing compounds such as sulfur- and oxygen-containing compounds like sulfates, sulfites and oxalates, as well as amine complexing agents and materials such as crown ethers.

In a second embodiment of the invention, fouling in equipment used to process a metal-containing naphthalenic feedstock mixture is reduced by treating the process stream of the naphthalenic feedstock mixture with a phosphorus-containing compound. Suitable phosphorus-containing compounds include both inorganic and organic phosphorus-containing materials, with inorganic phosphate salts often being preferred.

The term "metal-containing naphthalenic feedstock mixture" refers to a mixture containing at least 5 parts by weight of a naphthalenic compound and between about 10–40,000 total parts per million of one or more heavy metals having atomic numbers from 21 to 82.

Still another embodiment of the invention includes novel, low fouling compositions useful in the manufacture of aromatic materials compositions.

In yet another embodiment of the invention, processes for manufacturing aromatic carboxylates from alkyl- or acyl-substituted aromatic compounds are disclosed. These processes includes the steps of oxidizing an akyl- or acyl-substituted aromatic compound in the presence of one or more heavy metal catalysts to form aromatic acids of the alkyl- or acyl- substituted aromatic compound and then esterifying a reaction mixture containing the aromatic acids and heavy metal catalysts in the presence of a phosphorus-containing compound in an amount equal to about 0.1 to 2.0 moles of phosphorus, calculated as elemental phosphorus, per mole of heavy metal, calculated as elemental metal.

The foregoing processes are particularly well suited for minimizing fouling during the manufacture of dimethyl naphthalenedicarboxylates, and have been found to offer dramatic improvements in process equipment run times over processes which do not employs metal complexing compounds.

DETAILED DESCRIPTION OF THE INVENTION

We have discovered that treating process streams used to manufacture aromatic esters such as NDC with one or more metal complexing compounds greatly reduces fouling in process equipment. While our invention will be described in detail below in connection with an NDC manufacturing process, the invention is believed to be useful in other manufacturing processes using aromatic feedstocks, such as in the esterification or purification of terephthalic or isophthalic acid.

NDC manufacturing process streams can contain a wide variety of naphthalenic and other compounds. In a typical manufacturing process, NDA is mixed with an amount of methanol typically in excess of that which would be required to convert all of the carboxylic acid groups of NDA to methyl esters. This mixture is heated, with or without a catalyst, to form the dimethyl ester of NDA. The temperature used to form the dimethyl ester usually is about from 200 to about 700° F., and preferably about 500 to about 650° F. The product from this esterification reaction is purified by one or more crystallization, recrystallization and/or distillation steps to form purified NDC. Typically, to form highly pure NDC, a distillation step is required. Thus, the process streams used to manufacture NDC from NDA can range from a mixture comprising mostly NDA to mostly NDC, or mixtures thereof, and may include varying concentrations of methanol. The process streams also can comprise the monomethyl ester of NDA and other naphthalenic compounds. Several representative processes for preparing NDC from NDA are disclosed in U.S. Pat. Nos. 5,254,719; 5,262,560; and 5,350,874, the specifications of which are incorporated herein by reference.

Processes for preparing NDA feedstocks are described, for example, in U.S. Pat. No. 5,183,933, the specification of which also is incorporated herein by reference. NDC manufacturing process streams typically contain one or more heavy metals with atomic numbers ranging 21 to 82 that were used to catalyze the oxidation of a dialkylnaphthalene reactant. In many cases, NDA preferably is made by the liquid phase oxidation of 2,6-dimethylnaphthalene in the presence of cobalt and manganese oxidation catalysts. The crude NDA resulting from such an oxidation step may contain from about 10 parts per million by weight (ppm) to about 20,000 ppm, more typically about 500 ppm to about 10,000 ppm, and most typically from about 1000 ppm to about 6000 ppm of cobalt and manganese, calculated as elemental cobalt and elemental manganese.

When NDA containing the above-noted concentration of oxidation catalyst metals is used in processes for preparing NDC, the equipment used fouls rapidly. Typically fouled process equipment includes heat exchangers used for increasing the temperature of the process stream comprising NDA and methanol prior to the NDA esterification reaction, as well as reactors and piping used in connection with the esterification reaction. Metal-containing process streams also foul the filter surfaces used to filter NDC from crystallization and recrystallization solvents such as methanol, and foul internal portions of distillation columns used to fractionally distill NDC to form highly pure NDC. The term "foul" as used herein means the development or build-up of solids or other material on the working surfaces or internal passages of process equipment which results in an observable decrease in the capacity of the equipment. This development or build-up of material on such surfaces or in such passages results in a decrease in the efficiency of the operation of such equipment and eventually can result in inoperability of such equipment. As used herein, the term "inoperable" refers to a piece of equipment that has been fouled to a point that it functions at less than 60 percent of its rated capacity.

We discovered that the addition of one or more phosphorus-containing compounds to the aforementioned process streams greatly reduces or eliminates fouling of such process equipment. The amount of phosphorus-containing compound added is an amount that results in the reduction of the fouling of the process equipment. The amount of phosphorus-containing compound required to reduce fouling typically is at least about 0.1, preferably at least about 0.5, and more preferably at least about 0.8 moles of phosphorus, calculated as elemental phosphorus, per mole of total heavy metal, calculated as the elemental metal or metals, present in the process stream. Most preferably, the amount of phosphorus-containing compound added is an amount such that the mole ratio of phosphorus, calculated as elemental phosphorus, to the total of the heavy metal components, calculated as the elemental metal or metals, is about 1:1. Mole ratios which exceed about 1:1, however, have not been found to be detrimental to the purpose of this invention.

Phosphorus-containing compounds useful in the invention are any phosphorus-containing compounds that will reduce or prevent the fouling of the equipment. The term "phosphorus-containing compounds" as used herein includes both inorganic and organic compounds. If organic phosphorus-containing compounds are used, the compounds preferably are selected so that they have a low volatility. Inorganic phosphorus-containing compounds useful in the invention include monomeric phosphates, dimeric phosphates, and higher linear and cyclic polyphosphates, as well as the alkali metal salts and alkaline earth metal salts of these same phosphorus-containing compounds. Such compounds include, for example, $P_2O_5$, $H_3PO_4$, $H_4P_2O_7$, $H_5P_3O_{10}$, trimeta phosphoric acid, tetrameta phosphoric acid, one or more sodium phosphates such as, for example, $NaH_2PO_4$, $Na_2HPO_4$, $Na_3PO_4$, as well as hydrated versions thereof, and pyrophosphates such as sodium or potassium pyrophosphates. Mixtures of the foregoing are also well suited to use in the invention. Inorganic phosphates and salts thereof are a preferred source of phosphorus for the method of this invention. Organic phosphorus-containing compounds such as alkyl or aryl phosphates and phosphites also are believed to be suitable for use in the invention. For example, trimethyl phosphate, triphenyl phosphate, trimethyl phosphite, and triphenyl phosphite are believed to be useful.

Phosphorus-containing compounds can be added to one or more NDC manufacturing process streams at any suitable point. These streams can contain anywhere from about 1 to 99 parts, and more typically 5 to 70 parts, by weight of naphthalenic compounds. For example, the phosphorus-containing compound can be added to the process stream containing NDA and methanol, which stream is then reacted in an esterification reaction to form crude NDC. The phosphorus-containing compound also can be added to the methanol or to the NDA, or to the mixture of methanol and NDA.

The mixture of NDA and methanol so treated typically comprises about 5 to about 50 parts by weight NDA and about 50 to about 95 parts by weight methanol. The NDA used for such mixture typically contains about 10 ppm to about 20,000 ppm of heavy metal, typically cobalt and manganese, based on the weight of the metal. The molar ratio of cobalt to manganese therein typically is about 30:1 to about 1:30, more typically about 10:1 to 1:10, and most typically about 4:1 to 1:1. The amount of phosphorus-containing compound added is the amount stated hereinabove, based on the amount of heavy metal present in the process stream, i.e., at least about 0.1, preferably at least about 0.5, and more preferably at least about 0.8 mole of phosphorus, calculated as elemental phosphorus, per mole of heavy metal, calculated as the elemental metal.

While it is advantageous to add the phosphorus-containing compound to the process stream prior to the esterification reaction, the phosphorus-containing compound can be added at a later stage in the process to prevent fouling in downstream equipment such as the filters used to filter solutions of NDC or the distillation column used to distill NDC. The phosphorus-containing compound can be added in increments to the process stream or it can be added continuously. It can be added at more than one location in the process and either simultaneously or at different times, depending on the existing need to prevent fouling in the process equipment.

Addition of phosphorus-containing compound to various NDC process streams is illustrated by the following Examples.

EXAMPLE 1

A heat exchanger used to elevate the temperature of a mixture of NDC, NDA, and methanol to a temperature sufficient to melt the NDC was fouled and became inoperable after 72 hours of continuous operation. The mixture typically contained 30 wt. % methanol, 0.1 to 2 wt. % NDA, and about 1000 ppm to about 1300 ppm total cobalt and manganese, based on the weight of NDC.

The addition of from about 100 to about 500 ppm of phosphorus, based on the NDC content and added as sodium hexametaphosphate to the same mixture of NDC, NDA, and methanol, provided for the operation of the same exchanger for more than about 900 hours without fouling.

EXAMPLE 2

A filter used to recover crude crystalline NDC from a stream containing NDC, NDA, and methanol fouled and became inoperable after about 240 hours of continuous operation. This stream was obtained after cooling the total reactor effluent from the reactor used to esterify NDA with methanol. This mixture typically contained 20–30 wt. % NDC, 80–70 wt. % methanol, 0.1–2 wt. % NDA and monomethyl NDC, and from about 1000 ppm to about 1300 ppm total cobalt and manganese based on the weight of NDC present in the stream.

The addition of from about 100 ppm to about 600 ppm of phosphorus, based on the weight of NDC in the stream and added as sodium hexametaphosphate to the same mixture of NDC, NDA, and methanol, provided for the operation of the same filter for more than about 900 hours without fouling.

EXAMPLE 3

A heat exchanger used to elevate the temperature of a mixture of NDC, NDA, and methanol to a temperature sufficient to melt the NDC fouled and became inoperable after 72 hours of continuous operation. The mixture typically contained 30 wt. % methanol, 0.1 to 2 wt. % NDA, and 1700 ppm to about 2400 ppm total cobalt and manganese, based on the weight of NDC.

The addition of from about 300 to about 1900 ppm of phosphorus based on the NDC content, added as sodium dihydrogenphosphate to the same mixture of NDC, NDA, and methanol, provided for the operation of the same exchanger for more than about 900 hours without fouling.

EXAMPLE 4

A filter used to recover crude crystalline NDC from a stream containing NDC, NDA, and methanol was fouled after about 240 hours of continuous operation. This stream was obtained after cooling the total reactor effluent from the reactor used to esterify NDA with methanol. This mixture typically contained 20–30 wt. % NDC, 80–70 wt. % methanol, 0.1–2 wt. % NDA and monomethyl NDC, and from about 1700 ppm to about 2400 ppm total cobalt and manganese based on NDC.

The addition of from about 300 ppm to about 1900 ppm of phosphorus based on NDC and added as sodium dihydrogenphosphate to the same mixture of NDC, NDA, and methanol, provided for the operation of the same filter for more than about 900 hours without fouling.

The following prophetic Example 5 provides further guidance as to the use of our invention.

EXAMPLE 5

A reboiler is used to boil a mixture of NDC, monoesterified monomethyl 2,6-NDC, and NDA at approximately 500 degrees °F. fouls after less than 1000 hours of continuous operation. The mixture typically contains approximately 7% NDA, 20% monomethyl 2,6-NDC, 70% NDC, and about 3 to 4 total weight percent of cobalt and manganese.

About 0.7–1.3% of phosphorus is added, as sodium dihydrogen phosphate, to the same mixture and provides for operation of the same reboiler for more than about 1000 hours without fouling.

We believe similar results can be expected when using other phosphorus-containing compounds such as sodium hexametaphosphate, sodium dihydrogen phosphate, disodium hydrogen phosphate, trisodium phosphate, phosphoric acid, tripolyphosphates such as sodium tripolyphosphate, trimethyl phosphite, trimethyl phosphate, triphenyl phosphite, triphenyl phosphate and mixtures thereof.

While the foregoing Examples illustrate the particular utility of our invention with respect to the manufacture of NDC from NDA, we believe that the process is useful in connection with a wide variety of manufacturing processes in which a metal-containing aromatic feedstock mixture is reacted under aromatic feedstock processing conditions. Phosphorus-containing or other metal complexing compounds may be added to these processes in the same ratios and manners as discussed above in connection with the NDC based Examples.

As used herein, the term "metal-containing aromatic feedstock mixture" means a mixture containing at least 5 parts by weight of an aromatic compound and between 10–40,000 total parts per million of one or more heavy metals having atomic numbers from 21 to 82. The term "aromatic feedstock processing conditions" means an operating temperature of between about 100 to 750 degrees Fahrenheit and at operating pressures from between about 15 mm Hg absolute and about 1500 psia.

For example, the invention is to believed to be especially useful in processes for manufacturing aromatic carboxylates from alkyl- or acyl- substituted aromatic compounds which first oxidize an alkyl- or acyl substituted aromatic compound in the presence of one or more heavy metal catalysts to form aromatic acids of the alkyl- or acyl- substituted aromatic compound and which thereafter esterify a reaction mixture containing the aromatic acids and heavy metal catalysts. The use of a metal complexing compound such as a phosphorus-containing compound in an amount equal to about 0.1 to 2.0 moles of phosphorus calculated as elemental phosphorus per mole of heavy metal calculated as elemental metal should greatly minimize operational difficulties related to fouling equipment used in those processes such as filters, heat exchangers, and distillation columns. The following prophetic Examples illustrate the utility of the invention in some of these applications.

EXAMPLE 6

A heat exchanger used to elevate the temperature of a mixture of terephthalic acid (TA), dimethyl terephthalate (DMT) and methanol to a temperature sufficient to esterify the TA (typically about 500° F.) is fouled to the extent where heat transfer is significantly reduced. The mixture typically contains about 80 wt. % methanol, 16 wt. % TA, 4% recycle DMT, and about 50 ppm to about 200 ppm total cobalt and manganese, based on the weight of TA.

The addition of from about 25 to about 100 ppm of phosphorus based on the TA content, added as sodium hexametaphosphate to the same mixture of TA, DMT, and methanol greatly extends the operating time before the exchanger is significantly fouled.

EXAMPLE 7

A filter used to recover crude crystalline DMT from a stream containing DMT, TA, and methanol is fouled to the point where the filtration rate is seriously reduced. This stream is obtained after cooling the total reactor effluent from a reactor used to esterify TA with methanol. This mixture typically contains about 23 wt. % DMT, 75 wt. % methanol, 2 wt. % TA and monomethyl TA, and from about 50 ppm to about 200 ppm total cobalt and manganese based on the weight of DMT present in the stream.

The addition of from about 25 ppm to about 100 ppm of phosphorus based on the weight of DMT in the stream, added as sodium hexametaphosphate to the same mixture of DMT, TA and methanol extends the operating time before the filter is significantly fouled.

EXAMPLE 8

A heat exchanger used to elevate the temperature of a mixture of DMT, TA, and methanol to a temperature sufficient to dissolve the DMT is fouled to the extent where heat transfer is significantly reduced. The mixture typically contains 30 wt. % methanol, 0.1 to 2 wt. % TA, and 25 ppm to about 100 ppm total cobalt and manganese, based on the weight of DMT.

The addition of from about 25 to about 100 ppm of phosphorus based on the DMT content, added as sodium dihydrogen phosphate, to the same mixture of DMT, TA, and methanol, substantially extends the operating time before the filter is significantly fouled.

Additionally, while phosphorus-based compounds are the preferred compounds for treating metal-containing aromatic feedstock mixtures in accordance with our invention, we believe that the advantages of the invention may be realized using other metal complexing compounds. The term "metal complexing compound" means any compound that remains sufficiently stable under aromatic feedstock processing conditions to complex with the heavy metal or metals contained in an aromatic feedstock mixture to prevent fouling of the processing equipment. Such "metal complexing compounds" include, for example, phosphorus-containing compounds as well as other metal complexing compounds, for example, sulfur- and oxygen-containing compounds such as sulfates, sulfites and oxalates, as well as amine complexing agents and materials such as crown ethers.

While our invention has been discussed primarily in connection with the manufacture of aromatic esters such as dimethyl-2,6-naphthalene dicarboxylate, other applications will be apparent to those skilled in the art. Our invention, therefore, is intended to be limited only by the scope of the following claims.

We claim:

1. A method for reducing fouling in equipment used to process a metal-containing aromatic feedstock mixture containing at least 1 part by weight of an aromatic compound and between 10–40,000 total parts per million of one or more heavy metals having atomic numbers from 21 to 82, the method comprising treating a process stream of the aromatic feedstock mixture with a metal complexing compound.

2. The method of claim 1 wherein the aromatic compound in the metal-containing aromatic feedstock mixture comprises a compound selected from the group consisting of aromatic acids, aromatic esters, and mixtures thereof.

3. The method of claim 1 wherein the metal complexing compound is added in an amount equal to about 0.1 to 3.0 mole equivalents of metal complexing compound per mole of heavy metal calculated as elemental metal.

4. The method of claim 1 wherein the metal-containing aromatic feedstock mixture is processed under aromatic feedstock processing conditions, wherein the metal-containing aromatic feedstock mixture comprises between 1 and 99 total weight percent of naphthalene dicarboxylic acids and dimethyl naphthalene carboxylates, and wherein the metal complexing compound is a phosphorus-containing compound.

5. A method for reducing fouling in equipment used to process a metal-containing naphthalenic feedstock mixture containing at least 1 part by weight of a naphthalenic compound and between 10–40,000 total parts per million of one or more heavy metals having atomic numbers from 21 to 82, the method comprising treating a process stream of the naphthalenic feedstock mixture with a phosphorus-containing compound.

6. The method of claim 5 wherein the phosphorus-containing compound is added to the process stream in an amount equal to about 0.1 to 3.0 moles of phosphorus calculated as elemental phosphorus per mole of heavy metal calculated as elemental metal.

7. The method of claim 5 wherein the metal-containing naphthalenic feedstock mixture is processed under aromatic feedstock processing conditions, wherein the metal-containing naphthalenic feedstock mixture comprises between 1 and 99 total weight percent of naphthalene dicarboxylic acids and dimethyl naphthalene carboxylates, and wherein the heavy metals present in the mixture comprise at least 50 weight percent cobalt, manganese, or mixtures thereof, calculated as the weight percent of total heavy metals.

8. The method of claim 5 wherein the phosphorus-containing compound is selected from the group consisting of sodium hexametaphosphate, sodium dihydrogen phosphate, disodium hydrogen phosphate, trisodium phosphate, phosphoric acid, trimethyl phosphite, trimethyl phosphate, tripolyphosphates triphenyl phosphite, triphenyl phosphate and mixtures thereof.

9. The method of claim 5 wherein the metal-containing naphthalenic feedstock mixture comprises at least 5 weight percent methanol.

10. The method of claim 7 wherein the phosphorus-containing compound is selected from the group consisting of sodium hexametaphosphate, sodium dihydrogen phosphate, disodium hydrogen phosphate, trisodium phosphate, phosphoric acid, trimethyl phosphite, trimethyl phosphate, triphenyl phosphite, tripolyphosphates, triphenyl phosphate and mixtures thereof, and wherein the phosphorus-containing compound is added to the process stream in an amount equal to about 0.5 to 2.0 moles of phosphorus calculated as elemental phosphorus per mole of heavy metal calculated as elemental metal.

11. The method of claim 10 wherein the metal-containing naphthalenic feedstock mixture comprises at least 5 weight percent methanol.

12. A composition comprising 1 to 99 parts by weight of one or more naphthalenic materials, between 10–40,000 total parts per million of one or more heavy metals having atomic numbers from 21 to 82, and a phosphorus-containing compound in an amount equal to about 0.1 to 3.0 moles of phosphorus calculated as elemental phosphorus per mole of heavy metal calculated as elemental metal.

13. The composition of claim 12 wherein the heavy metal comprises between about 1000 and 6000 total parts per million of cobalt, manganese, or mixtures thereof.

14. The composition of claim 12 wherein the phosphorus-containing compound is selected from the group consisting of hexametaphosphate and salts thereof.

15. The composition of claim 13 wherein the phosphorus-containing compound is selected from the group consisting of sodium hexametaphosphate, sodium dihydrogen phosphate, disodium hydrogen phosphate, trisodium phosphate, phosphoric acid, trimethyl phosphite, trimethyl phosphate, tripolyphosphates, triphenyl phosphite, triphenyl phosphate, and mixtures thereof, and wherein the phosphorus-containing compound is added to the process stream in an amount equal to about 0.5 to 2.0 moles of phosphorus calculated as elemental phosphorus per mole of heavy metal calculated as elemental metal.

16. The composition of claim 12 further comprising between about 5 to 50 parts by weight of 2,6-naphthalenedicarboxylic acid and 50 to 95 parts by weight of methanol.

17. The composition of claim 16 wherein the phosphorus-containing compound is selected from the group consisting of sodium hexametaphosphate, sodium dihydrogen phosphate, disodium hydrogen phosphate, trisodium phosphate, phosphoric acid, trimethyl phosphite, trimethyl phosphate, tripolyphosphates, triphenyl phosphite, triphenyl phosphate, and mixtures thereof, and wherein the phosphorus-containing compound is present in an amount equal to about 0.5 to 2.0 moles of phosphorus calculated as elemental phosphorus per mole of heavy metal calculated as elemental metal.

18. A process for manufacturing aromatic carboxylates from alkyl- or acyl- substituted aromatic compounds comprising the steps of:

oxidizing an alkyl- or acyl- substituted aromatic compound in the presence of one or more heavy metal catalysts to form aromatic acids of the alkyl- or acyl- substituted aromatic compound; and thereafter esterifying a reaction mixture containing the aromatic acids and heavy metal catalysts in the presence of a phosphorus-containing compound in an amount equal to about 0.1 to 2.0 moles of phosphorus calculated as elemental phosphorus per mole of heavy metal calculated as elemental metal.

19. The process of claim 18 wherein the substituted aromatic compound comprises dimethyl naphthalene, and wherein the heavy metals present in the reaction mixture comprise between about 1000 to 6000 ppm of the reaction mixture.

20. The process of claim 18 wherein the reaction mixture of the esterifying step includes between 50 and 95 parts by weight of methanol and between about 5 and 50 parts by weight of 2,6-naphthalene dicarboxylic acid.

21. The method of claim 8 wherein the tripolyphosphate is sodium tripolyphosphate.

22. The method of claim 10 wherein the tripolyphosphate is sodium tripolyphosphate.

23. The composition of claim 15 wherein the tripolyphosphate is sodium tripolyphosphate.

24. The composition of claim 17 wherein the tripolyphosphate is sodium tripolyphosphate.

* * * * *